United States Patent
Satoda et al.

(10) Patent No.: US 8,506,991 B2
(45) Date of Patent: Aug. 13, 2013

(54) NICOTINE TRANSDERMAL PREPARATION AND PRODUCTION METHOD THEREOF

(75) Inventors: Shiro Satoda, Ibaraki (JP); Kazuhisa Ninomiya, Ibaraki (JP); Junichi Saito, Ibaraki (JP); Kensuke Matsuoka, Ibaraki (JP); Shunetsu Kikuchi, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 1103 days.

(21) Appl. No.: 11/546,302

(22) Filed: Oct. 12, 2006

(65) Prior Publication Data

US 2007/0087043 A1    Apr. 19, 2007

(30) Foreign Application Priority Data

Oct. 13, 2005   (JP) .................................. 2005-299203

(51) Int. Cl.
*A61L 15/16*   (2006.01)
*A61K 9/70*    (2006.01)
*A61K 31/465*  (2006.01)
*A61K 47/14*   (2006.01)

(52) U.S. Cl.
CPC ............. *A61K 9/7061* (2013.01); *A61K 31/465* (2013.01); *A61K 47/14* (2013.01)
USPC ....................................................... 424/448

(58) Field of Classification Search
USPC ......................................................... 424/449
See application file for complete search history.

(56) References Cited

U.S. PATENT DOCUMENTS 4,597,961 A   7/1986   Etscorn
4,687,481 A   8/1987   Nuwayser (Continued)

FOREIGN PATENT DOCUMENTS

EP   1 736 146   12/2006
JP   2708391     10/1997

(Continued)

OTHER PUBLICATIONS

English Translation of Russian Office Action in RU 2006136140, received Apr. 26, 2010.

(Continued)

*Primary Examiner* — Brian Gulledge
(74) *Attorney, Agent, or Firm* — Wenderoth, Lind & Ponack, L.L.P.

(57) ABSTRACT

The present invention provides a production method of a nicotine transdermal preparation, which is capable of producing a nicotine transdermal preparation conveniently and economically, while maintaining highly precise content uniformity, which is capable of producing a preparation simultaneously achieving fixedness and a soft feeling during adhesion, associated with reduced skin irritation upon peeling off and superior in adhesive property. The present invention provides a nicotine transdermal preparation superior in content uniformity, simultaneously achieving fixedness and a soft feeling during adhesion, and showing reduced skin irritation upon peeling off.

The present invention provides a method of producing a preparation containing a support and an adhesive layer formed thereon, which adhesive layer containing nicotine and a liquid ingredient compatible with the adhesive, which method includes (1) providing the adhesive layer wherein a contact angle of nicotine with the adhesive layer before containing nicotine is 20-60°, and (2) applying nicotine to the adhesive layer to allow absorption of nicotine into the adhesive layer, as well as a preparation containing a support and an adhesive layer formed thereon, which adhesive layer including nicotine and a liquid ingredient compatible with the adhesive, wherein a contact angle of nicotine with the adhesive layer before containing nicotine is 20-60°.

5 Claims, 4 Drawing Sheets

(56) References Cited

U.S. PATENT DOCUMENTS

| | | | |
|---|---|---|---|
| 4,946,853 A | 8/1990 | Bannon et al. | |
| 5,302,395 A * | 4/1994 | Ebert et al. | 424/449 |
| 6,139,868 A | 10/2000 | Hoffmann | |
| 7,029,692 B1 | 4/2006 | Bracht | |
| 2001/0006628 A1 * | 7/2001 | Govil et al. | 424/78.31 |
| 2003/0009139 A1 * | 1/2003 | Hori et al. | 604/307 |
| 2004/0096490 A1 | 5/2004 | Bracht et al. | |
| 2004/0161454 A1 * | 8/2004 | Schink et al. | 424/449 |
| 2005/0244486 A1 * | 11/2005 | Caldwell et al. | 424/449 |
| 2006/0286160 A1 | 12/2006 | Satoda et al. | |
| 2007/0026055 A1 * | 2/2007 | Ninomiya et al. | 424/449 |

FOREIGN PATENT DOCUMENTS

| | | |
|---|---|---|
| JP | 2763773 | 3/1998 |
| JP | 11-502840 | 3/1999 |
| JP | 3035346 | 2/2000 |
| JP | 2002-531488 | 9/2002 |
| JP | 2002-535475 | 10/2002 |
| JP | 2007-31427 | 2/2007 |
| KR | 10-2006-0133900 | 12/2006 |
| KR | 10-2007-0015874 | 2/2007 |
| RU | 2 124 340 | 1/1999 |
| WO | 88/01516 | 3/1988 |
| WO | 89/07429 | 8/1989 |
| WO | 91/16085 | 10/1991 |
| WO | 93/00057 | 1/1993 |
| WO | 93/00058 | 1/1993 |
| WO | 94/04109 | 3/1994 |
| WO | 95/24172 | 9/1995 |
| WO | 96/08229 | 3/1996 |
| WO | 96/25923 | 8/1996 |
| WO | 96/30001 | 10/1996 |
| WO | 00/33812 | 6/2000 |
| WO | 00/37058 | 6/2000 |
| WO | 00/44846 | 8/2000 |
| WO | 00/57824 | 10/2000 |
| WO | 02/069940 | 9/2002 |
| WO | 1 749 521 | 2/2007 |

OTHER PUBLICATIONS

Japanese Office Action entitled Notice of Reasons for Refusal (together with English translation) mailed Dec. 13, 2011, in corresponding Japanese Application No. 276913/2006.

Taiwanese Office Action (together with English translation) dated Apr. 13, 2012, issued in corresponding Taiwanese Application No. 101-2(5)01109-10120353940.

Canadian Office Action issued Dec. 6, 2012 in corresponding Canadian Application No. 2,563,496.

Korean Office Action issued Feb. 20, 2013 in corresponding Korean Application No. 10-2006-0099816, with English translation.

* cited by examiner

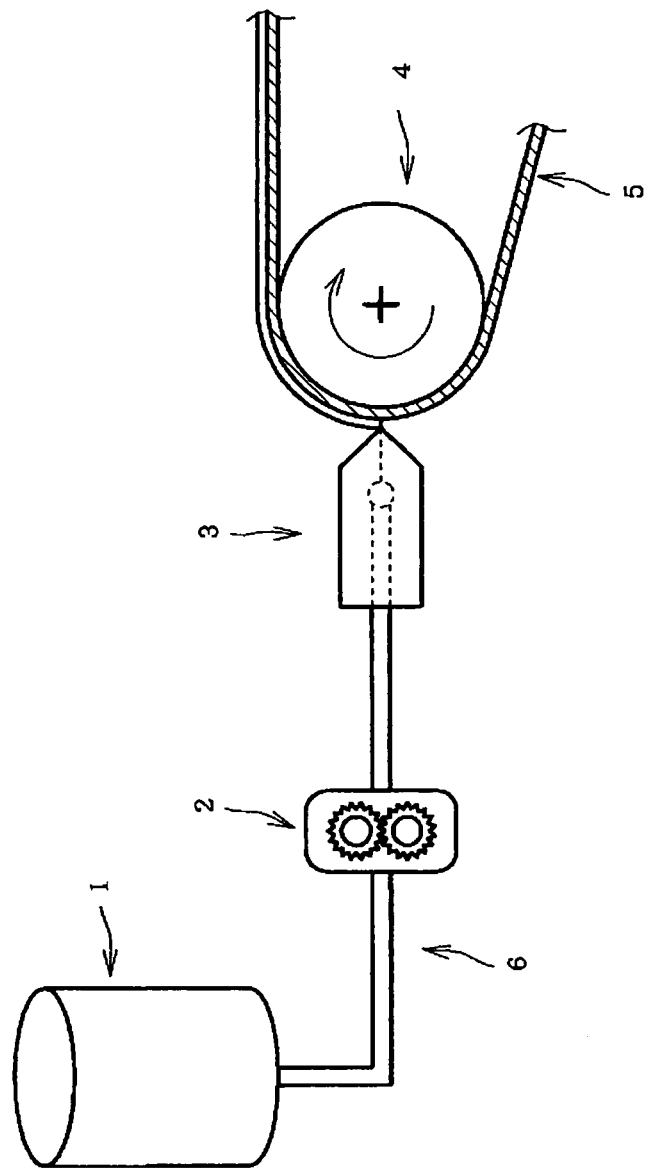
FIG. 1-A

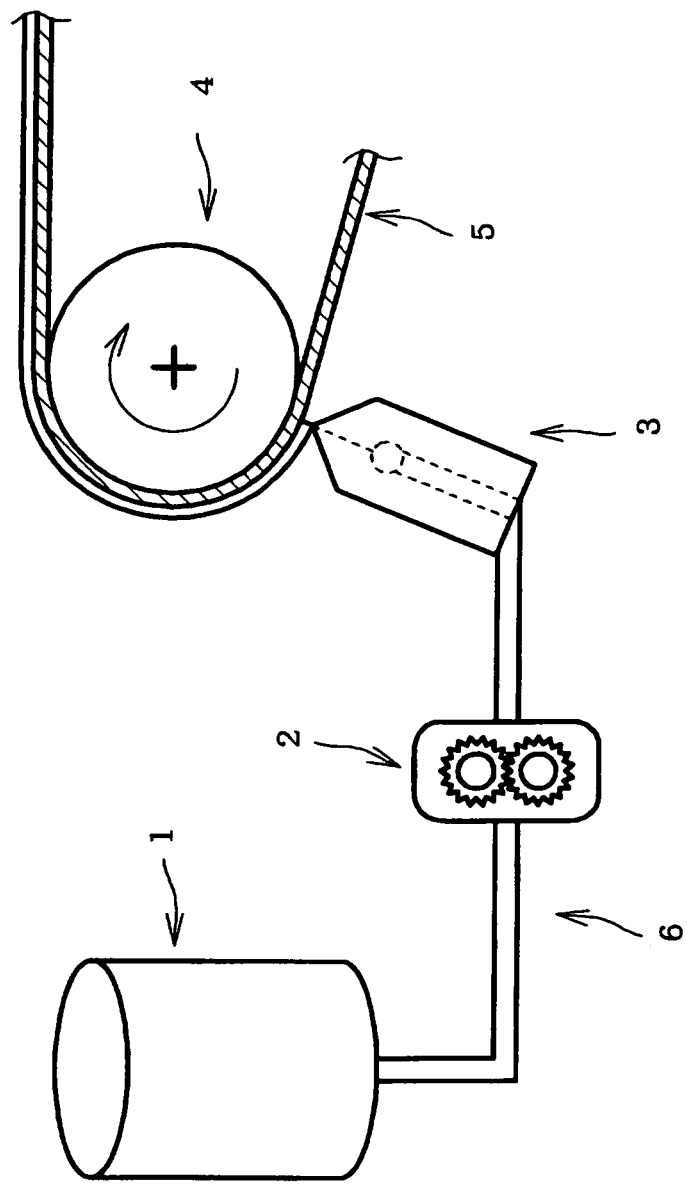
FIG. 1-B

NICOTINE TRANSDERMAL PREPARATION AND PRODUCTION METHOD THEREOF

TECHNICAL FIELD OF THE INVENTION

The present invention relates to nicotine transdermal preparations to be applied to the outer skin to allow transdermal absorption of nicotine into the body and production methods thereof.

BACKGROUND OF THE INVENTION

It is well known that nicotine contained in cigarettes is deeply involved in habitual smoking. As a method for reducing smoking, administration of nicotine in a form other than smoking into the living organism has been proposed to suppress habitual smoking, and various nicotine administration methods have been proposed with the growing antismoking mood in the world. These methods are called what is called a nicotine supplement therapy, which includes the following methods.

One of them is a method of administering nicotine contained in a chewing gum or drug lozenge into the body from the mouth cavity. According to this administration method, in fact, a large amount of nicotine is swallowed down with the saliva, by which the nicotine is mostly metabolized and cleared from the blood during passage through the liver as in the case of oral administration of general drugs, and a high effect cannot be expected. Moreover, since this method is a temporary administration method, frequent application is necessary and, since nicotine directly touches the inner wall of the mouth and esophagus, uncomfortable side effects such as bad taste, heartburn, nausea, hiccup and the like are caused.

There is another method wherein a nicotine-containing solution is placed in a plastic one-time container or multiple-time use container, which is then inserted into a nostril for direct administration of the nicotine solution in the container through the nasal mucous membrane. However, this method is not preferable from a hygiene standpoint, since the container directly contacts the nasal mucous membrane. In addition, handling and management is difficult. Moreover, since only a temporary effect is expected as in the above method, frequent administration is necessary. In particular, this method is problematic since it includes insertion of the container into the nostril, which makes administration in front of others embarrassing, and the like.

In contrast to the above-mentioned two administration methods, various transdermal preparations have recently been developed, which aim at administering nicotine transdermally. Many patent applications directed to transdermal preparations have been filed, some of which have already been put to practice as preparations.

While general advantages of the transdermal preparation are already known widely, when applied to administration of nicotine, in particular, the preparation can resolve almost all the shortcomings of the above-mentioned two administration methods. The greatest merit of the preparation is considered to reside in the fact that the blood concentration can be maintained at a constant level for a long time after adhesion of the preparation, which decreases the trouble of administration.

However, the existing transdermal preparations of nicotine have the following problems.

For use of these nicotine transdermal preparations, a stop-smoking program has been set to quit smoking, and the program generally requires once-a-day adhesion for several weeks. The major side effects of this administration method include topical side effects such as itching, erythema and the like. To avoid skin irritation, therefore, package inserts of the preparations contain a written instruction to change the adhesion site every time of application. Furthermore, the skin irritation developed by peeling off of the preparation cannot be ignored, since the preparation needs to be exchanged every day. Accordingly, the development of a preparation causing less irritation has been desired.

As the adhesive currently used for the nicotine transdermal preparations, rubber adhesives represented by polyisobutylene (PIB) and styrene-isoprene-styrene block copolymer (SIS), and acrylic adhesives made of a copolymer of acrylic monomers can be mentioned. Of these, for PIB adhesive, a technique including mixing a high molecular weight component and a low molecular weight component to impart good adhesiveness to the human skin and cohesion (e.g., JP-B-3035346) is available. However, to achieve good skin adhesion, cohesion needs to be sacrificed somewhat and, when adhesiveness is preferentially considered, a problem occurs in that an adhesive flows out from the edge of a preparation during preservation due to the decreased cohesion, thus causing a cold flow (low temperature flow). The cold flow invites difficulty in taking out the preparation from the packaging material due to the attachment of adhesive in the packaging material. Particularly, since nicotine has a strong plasticizing action on the adhesive, the above-mentioned cold flow phenomenon remarkably expresses in a nicotine transdermal preparation. While normal rubber adhesives adhere well to the dry skin, since adhesives have low hydrophilicity, sweat is pooled in the interface between the skin and the adhesion surface during application, which may lift the adhesive and cause delamination, thus resulting in falling off during use. Furthermore, the sweat develops stuffiness to easily cause irritation, and a feeling during adhesion is not necessarily good.

On the other hand, a nicotine transdermal preparation containing an acrylic adhesive is associated with a problem of skin irritation caused by peeling off for exchange of the preparation. Moreover, since the preparation contains a non-woven fabric or paper inserted in its adhesive layer as an auxiliary material for applying liquid nicotine to the adhesive layer during production, the whole preparation is thick, physical irritation easily occurs during application due to the rough feeling of the preparation, and a feeling during adhesion is not necessarily good.

Nicotine is a highly volatile and highly toxic drug, where volatilization of nicotine has a risk of increasing the safety risk and the burden on the environment. Accordingly, various production methods of nicotine transdermal preparations in consideration of this point have been known.

JP-A-2002-531488 discloses a production method of a transdermal patch, which comprises using a hexane solvent having a low boiling point to prepare a coating solution for a silicone adhesive, and applying the solution at a low temperature to decrease the decomposition or loss of a liquid drug of nicotine and the like. While this method employs coating at a low temperature, it cannot completely eliminate the possibility of loss of nicotine, and may require charging of an increased amount and the like to achieve the desired amount of nicotine. In addition, since silicone adhesives are expensive, this method is disadvantageous from an economical aspect.

JP-A-11-502840 discloses a continuous production method of a pressure-sensitive skin adhesive sheet material containing a liquid, which comprises combining a coating medium containing the liquid and a polymer base layer, wherein nicotine is exemplified as a liquid drug to be contained. The liquid application in this case is characterized in that a polymer component is contained in the coating medium, where it is described that direct and uniform application of the nicotine liquid without processing was tried, namely, at 0% content of the polymer, but failed. The description suggests difficulty in applying nicotine as it is to an adhesive layer even by those of ordinary skill in the art.

JP-B-2708391 discloses a production method of a skin permeability administration tool comprising an absorption material such as a non-woven fabric impregnated with highly volatile nicotine, and adhesive layers sandwiching the substance. It is described that the main non-woven fabric layer to be used permits printing of nicotine, and does not function as a drug reservoir. According to this method, the preparation becomes thick due to the non-woven fabric sandwiched in the plaster, which may impair a soft feeling of the preparation and influence adhesion of the preparation. The preparation is economically disadvantageous in that the production cost becomes high.

JP-B-2763773 discloses a production method of a treating product, by introducing a depot containing an active substance such as nicotine and the like into a reservoir matrix of an adhesive and the like. In the example of this reference, the depot containing nicotine contains EUDRAGIT E 100. The depot is added to a non-woven fabric to give a plaster, where the non-woven fabric as an inactive auxiliary substance helps uniform dispersion of nicotine. This reference does not disclose a technique to apply nicotine without using an inactive auxiliary substance.

While various publications are known as regards nicotine transdermal preparations as mentioned above, they contain no disclosure relating to adhesive property and handling property.

DISCLOSURE OF THE INVENTION

The present invention provides a production method of a nicotine transdermal preparation, which is capable of producing a nicotine transdermal preparation continuously, conveniently and economically, while maintaining highly precise content uniformity, and the production method of a nicotine transdermal preparation capable of producing a preparation simultaneously achieving fixedness and a good feeling (a soft feeling) during adhesion, associated with reduced skin irritation upon peeling off and superior in adhesive property. In addition, the present invention aims at providing a nicotine transdermal preparation superior in content uniformity, which simultaneously achieves fixedness and a good feeling (a soft feeling) during adhesion, and shows superior adhesive properties and reduced skin irritation upon peeling off.

The present inventors have conducted intensive studies in an attempt to solve the aforementioned problems and found that the above-mentioned object can be achieved by adjusting the contact angle of nicotine to an adhesive layer to 20-60° before containing nicotine (i.e., before nicotine application), which resulted in the completion of the present invention.

Accordingly, the present invention provides the following.

[1] A nicotine transdermal preparation comprising a support and an adhesive layer formed thereon, which adhesive layer comprising nicotine and a liquid ingredient compatible with the adhesive, wherein a contact angle of nicotine with the adhesive layer before containing nicotine is 20-60°.

[2] The preparation of the above-mentioned [1], wherein the liquid ingredient compatible with the adhesive is contained in a proportion of 20-65 wt % relative to the adhesive layer.

[3] The preparation of the above-mentioned [1] or [2], wherein the adhesive layer is a crosslinked acrylic adhesive layer.

[4] The preparation of any one of the above-mentioned [1]-[3], wherein the contact angle of nicotine with the adhesive layer before containing nicotine changes by not less than 15% between one second after dropwise addition of nicotine and 3 minutes after the dropwise addition of nicotine.

[5] A method of producing a nicotine transdermal preparation comprising a support and an adhesive layer formed thereon, which adhesive layer comprising nicotine and a liquid ingredient compatible with the adhesive, which comprises providing the adhesive layer wherein a contact angle of nicotine with an adhesive layer comprising a liquid ingredient compatible with the adhesive, which is before containing nicotine, is 20-60°, and applying nicotine to the adhesive layer to allow absorption of nicotine into the adhesive layer.

[6] The method of the above-mentioned [5], wherein the liquid ingredient compatible with the adhesive is contained in a proportion of 20-65 wt % relative to the adhesive layer.

[7] The method of the above-mentioned [5] or [6], wherein the adhesive layer is a crosslinked acrylic adhesive layer.

[8] The method of any one of the above-mentioned [5]-[7], wherein the contact angle of nicotine with the adhesive layer before containing nicotine changes by not less than 15% between one second after dropwise addition of nicotine and 3 minutes after dropwise addition of nicotine.

BRIEF DESCRIPTION OF THE DRAWINGS

FIG. 1A is a schematic showing of one preferable embodiment wherein nicotine is applied to an adhesive layer.

FIG. 1B is a schematic showing of one preferable embodiment wherein nicotine is applied to an adhesive layer.

Figure 2:
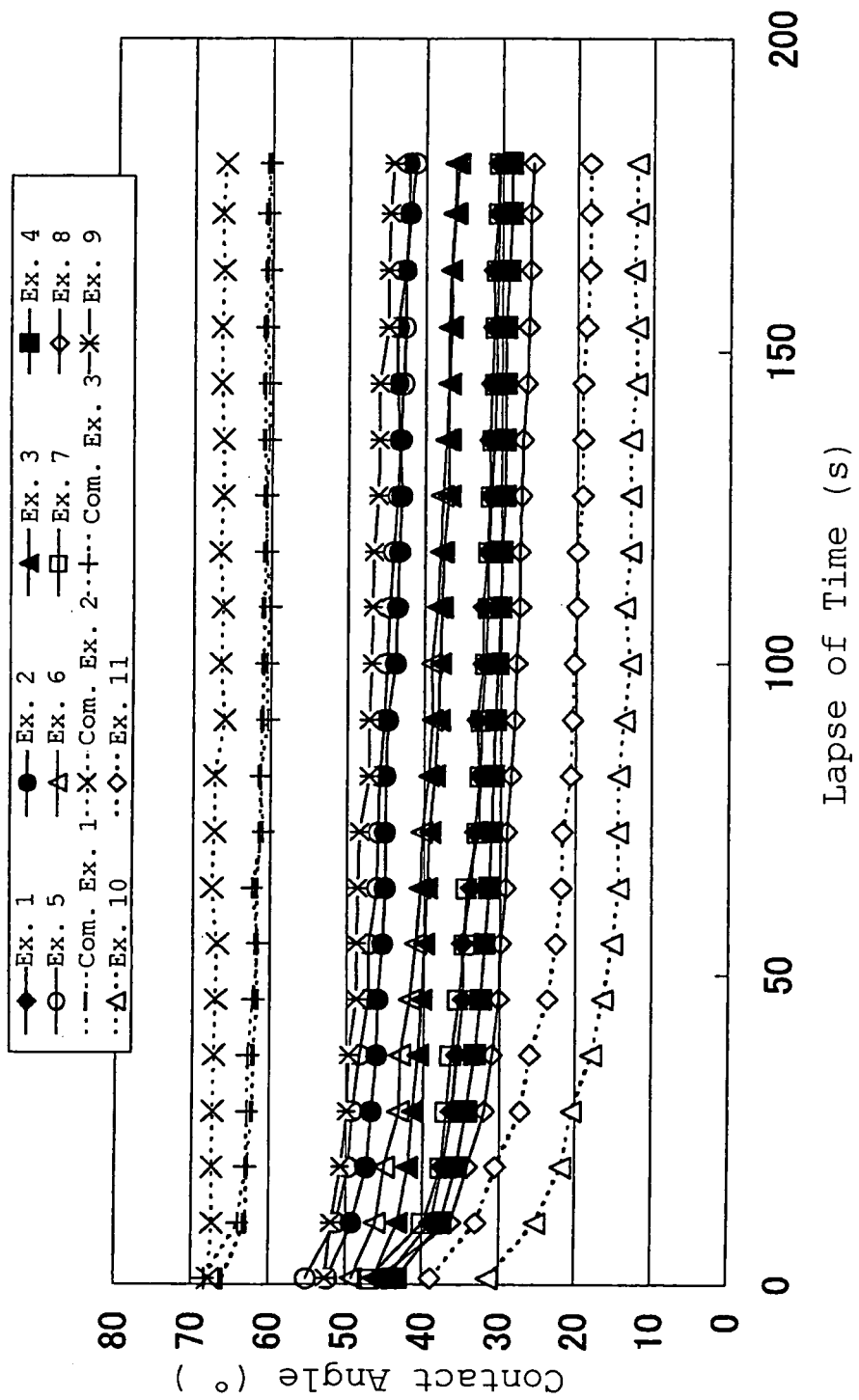
FIG. 2 is a graph showing the measurement results (time-course change) of the contact angle of nicotine with the adhesive layers of Examples 1-11 and Comparative Examples 1-3, in Experimental Example.

In the FIG. 1 is a nicotine supply tank, 2 is a measuring pump, 3 is a die, 4 is a backup roll, 5 is an adhesive layer and 6 is a nicotine supply line.

EFFECT OF THE INVENTION

According to the production method of the nicotine transdermal preparation of the present invention, by adjusting the contact angle of nicotine with an adhesive layer before nicotine application to fall within the range of 20-60°, nicotine is not repelled on the adhesive surface, nicotine can be directly and uniformly applied to the adhesive layer, and nicotine transdermal preparations can be produced continuously while maintaining highly precise content uniformity. In addition, the method of the present invention is convenient since it does not require a complicated step such as insertion of conventional non-woven fabric and the like. Furthermore, since the method of the present invention does not necessarily require an expensive material such as a conventional silicone adhesive, it is economically advantageous. Moreover, the thus-obtained nicotine transdermal preparation of the present invention shows superior content uniformity, superior adhesive property to afford a good feeling (a soft feeling) during adhesion and reduced skin irritation upon peeling off, as compared to conventional preparations.

BEST MODE FOR EMBODYING THE INVENTION

The nicotine transdermal preparation of the present invention comprises a support and an adhesive layer formed thereon, which contains nicotine and a liquid ingredient compatible with the adhesive, wherein the contact angle when a nicotine droplet is contacted with the adhesive layer before containing nicotine is 20-60°.

In the present specification, the "contact angle" means a contact angle when a nicotine droplet in a droplet amount of 1.1 μL is contacted with an adhesive surface and the contact angle is measured one second later under the conditiyions of room temperature 23±2° C. and relative humidity 60±10% RH, unless otherwise specified.

As used herein, the contact angle of nicotine with an adhesive layer is specifically measured as follows.

A sample is fixed on a glass slide with an adhesive surface of its adhesive layer facing upward, and the slide is set on an apparatus. A nicotine droplet (1.1 μL) is contacted with the adhesive surface, and the contact angle after one second is measured under the above-mentioned conditions. Changes in the contact angle are measured with time at every 9 seconds for 3 minutes.

Conveniently, the above-mentioned contact angle is measured using a contact angle measurement apparatus Drop-Master 700 manufactured by Kyowa Interface Science Co., LTD.

As mentioned below, the nicotine transdermal preparation of the present invention is produced by forming an adhesive layer containing a liquid ingredient compatible with the adhesive on a support or release liner and applying nicotine to the adhesive surface of the adhesive layer. As the result of absorption of the applied nicotine into the adhesive layer, an adhesive layer containing nicotine and a liquid ingredient compatible with the adhesive is formed on the support or release liner. The "adhesive layer before containing nicotine" means an adhesive layer before application of nicotine in the production step of the preparation; in other words, an adhesive layer containing a liquid ingredient compatible with the adhesive and a pharmaceutically acceptable additive where desired.

As mentioned above, the nicotine transdermal preparation of the present invention characteristically shows a contact angle of 20-60° when a nicotine droplet is brought into contact with an adhesive layer before containing nicotine.

When the contact angle is greater than 60°, the applied nicotine is repelled on the adhesive surface, failing to provide uniform application. As a result, the preparation fails to achieve good content uniformity. When the contact angle is smaller than 20°, the ratio of the liquid component needs to be markedly increased. As a result, adhesive properties such as adhesive force, coagulation, tack and the like become ill-balanced, possibly causing peeling off and adhesive residue. The contact angle is more preferably within the range of 25-55°, particularly preferably within the range of 25-50°, and still more preferably within the range of 40-55°.

For stable production of the nicotine transdermal preparation by uniform application of nicotine to an adhesive layer, the applied nicotine is preferably rapidly absorbed into the adhesive layer. Since nicotine added dropwise to an adhesive surface is absorbed into the adhesive, the contact angle changes (decreases) with time. A greater time-course decrease (change) in the contact angle is generally more preferable for uniform application of nicotine.

In the present invention, the change in the contact angle of nicotine with an adhesive layer before containing nicotine from one second after dropwise addition of nicotine to 3 minutes after the dropwise addition of nicotine is preferably not less than 15%, more preferably not less than 20%. The change in the contact angle from one second after dropwise addition of nicotine to 3 minutes after the dropwise addition of nicotine is defined by the following formula.

Change (%) in contact angle={(change (°) in contact angle)/(contact angle after 1 second)}×100 wherein change (°) in contact angle=(contact angle after 1 second)−(contact angle after 3 minutes)

When the change (%) in the contact angle does not reach 15%, a uniform application of nicotine to an adhesive layer may become difficult during production of nicotine transdermal preparations, which in turn possibly prevents good content uniformity of the preparation.

For nicotine to be absorbed by an adhesive layer, a certain amount of time may be necessary. In this event, it is desirable during operation in the production step that nicotine does not flow off from the surface of the adhesive layer immediately after application, but stays on the surface of the adhesive layer for 3 minutes after the start of the nicotine application. The present invention takes note of such contact angles of nicotine with the adhesive layer, which fall within the above-mentioned range at any point in time from one second to 180 seconds from the start of the contact. It is preferable that the contact angles fall within the above-mentioned range at any point in time from one second to 180 seconds from the start of the contact. This enables a markedly easy application of nicotine to an adhesive layer surface.

A nicotine transdermal preparation wherein a contact angle of nicotine with an adhesive layer before containing nicotine is 20-60°, particularly, a nicotine transdermal preparation wherein the contact angle is 20-60°, and the contact angle changes by not less than 15% between one second after dropwise addition of nicotine and 3 minutes after the dropwise addition of nicotine, can be afforded by the presence of a liquid ingredient compatible with the adhesive in the adhesive layer.

Since nicotine shows the same level of viscosity as does water at ambient temperature, it is repelled by general adhesive layers and the contact angle becomes large. In the present invention, the above-mentioned preferable range of contact angle can be achieved by the presence of a liquid component in an adhesive layer.

The nicotine to be used in the present invention is desirably liquid at ambient temperature, and preferably a nicotine free base, from the aspect of transdermal absorbability and direct application.

While the amount of nicotine to be contained in an adhesive layer can be appropriately determined according to the administration object, it is generally preferably about 10-40 wt %, more preferably about 15-30 wt %, relative to the adhesive layer. When the content is less than 10 wt %, nicotine release in an amount necessary to achieve a sufficient treatment effect may not be possibly expected, and when it exceeds 40 wt %, the treatment effect is limited, an economical disadvantage is produced, and skin irritation due to nicotine may possibly be expressed.

In the present invention, moreover, drugs other than nicotine may be contained in an adhesive layer, as long as no adverse influence is exerted on the desired use and practice of the present invention. As such drugs, for example, Mecamylamine, pempidine and the like as nicotine antagonists can be mentioned.

The adhesive to be used in the present invention may be those generally used in the field of transdermal preparation, such as rubber adhesives, vinyl adhesives, acrylic adhesives and the like. An adhesive permitting a crosslinking treatment is preferable.

As the rubber adhesive, for example, adhesives containing silicone rubber, polyisoprene rubber, polyisobutylene rubber, styrene-butadiene rubber, styrene-isoprene-styrene block copolymer rubber, styrene-butadiene-styrene block copolymer rubber and the like as a main component can be mentioned.

As the vinyl adhesive, for example, adhesives containing polyvinyl alcohol, polyvinyl alkyl ether, polyvinyl acetate and the like as a main component can be mentioned.

While the acrylic adhesive is not particularly limited, since crosslinking treatment is easy, a copolymer wherein (meth)acrylic acid alkyl ester has been copolymerized as a main component is preferably used. As (meth)acrylic acid alkyl ester, those wherein the alkyl group is a linear, branched chain or cyclic alkyl group having 4 to 18 carbon atoms (e.g., butyl, pentyl, hexyl, heptyl, octyl, nonyl, decyl, undecyl, dodecyl, tridecyl, 2-ethylhexyl, cyclohexyl etc.) are preferable. Such (meth)acrylic acid alkyl esters can be used in a combination of one or more kinds thereof. Of these, monomers that lower the glass transition temperature are preferable to afford adhesiveness at ambient temperature, and (meth)acrylic acid alkyl esters wherein the alkyl group is a linear or branched chain or cyclic alkyl group having 4 to 8 carbon atoms (e.g., butyl, pentyl, hexyl, heptyl, octyl, 2-ethylhexyl, cyclohexyl etc., preferably butyl, 2-ethylhexyl, cyclohexyl, particularly preferably 2-ethylhexyl) are more preferable. As the (meth)acrylic acid alkyl esters wherein the alkyl group has 4-8 carbon atoms, butyl acrylate, 2-ethylhexyl acrylate, 2-ethylhexyl methacrylate, cyclohexyl acrylate and cyclohexyl methacrylate are preferable, and 2-ethylhexyl acrylate is most preferable.

As the second component to be copolymerized with the above monomer, a monomer having a functional group capable of being involved in a crosslinking reaction may be used. A vinyl monomer having hydroxy group or carboxyl group as a functional group is preferably used in the present application. As the monomer of the second component, specifically, hydroxyethyl (meth)acrylate (e.g., 2-hydroxyethyl acrylate), hydroxypropyl (meth)acrylate, (meth)acrylic acid, itaconic acid, maleic acid, methaconic acid, citraconic acid, glutaconic acid and the like can be mentioned. These second monomer components can be used in combination of one or more kinds thereof.

A tertiary monomer component other than the second monomer component may be copolymerized. It can be used for adjusting cohesion of the adhesive layer, and adjusting solubility or releasability of nicotine or combined drug. As the tertiary monomer component, for example, vinyl esters such as vinyl acetate, vinyl propionate and the like; vinyl ethers such as methyl vinyl ether, ethyl vinyl ether and the like; vinyl amides such as N-vinyl-2-pyrrolidone, N-vinyl caprolactam and the like; hydroxy group-containing monomers such as (meth)acrylic acid alkyl ester, hydroxypropyl (meth)acrylate, α-hydroxymethyl acrylate and the like; amido group-containing monomers such as (meth)acrylamide, dimethyl(meth)acrylamide and the like; alkoxy group-containing monomers such as (meth)acrylic acid methoxyethyl ester, (meth)acrylic acid ethoxyethyl ester and the like; vinyl monomers such as styrene, vinyl pyridine, vinyl imidazole, vinyl morpholine and the like; and the like can be mentioned. These tertiary monomer components can be used in combination of one or more kinds thereof.

In the present invention, when a copolymer of the above-mentioned (meth)acrylic acid alkylester and the above-mentioned second monomer component is used as an acrylic adhesive, for example, a copolymer containing (meth)acrylic acid alkylester:second monomer=about 40-99.9:0.1-10 (weight ratio) can be used, without any particular limitation.

Moreover, when the above-mentioned tertiary monomer component is used, for example, a copolymer containing (meth)acrylic acid alkyl ester:second monomer:tertiary monomer=about 40-99.9:0.1-10:0-50 (weight ratio) can be used, without any particular limitation.

Such copolymers can be obtained by a polymerization method known per se. For example, they can be obtained by adding a polymerization initiator (e.g., benzoyl peroxide, 2,2'-azobisisobutyronitrile etc.) to the above-mentioned monomer and reacting the mixture in a solvent (e.g., ethyl acetate etc.) at 50-70° C. for 5-48 hr.

As the adhesive, silicone rubbers and acrylic adhesives are preferable, since a crosslinking treatment can be easily carried out using a crosslinking agent.

In the present invention, a crosslinked acrylic adhesive is preferably used as an adhesive.

In the present invention, a liquid ingredient compatible with the adhesive is contained in an adhesive layer. The liquid ingredient imparts a soft feeling by plasticizing an adhesive, and reduces pain caused by skin adhesion during peeling off the nicotine transdermal preparation from the skin and skin irritation. In addition, it adjusts wettability of nicotine relative to an adhesive, and decreases the contact angle to enable direct application of nicotine to the adhesive layer. Accordingly, as the liquid component, any liquid substance can be used as long as it shows a plasticized action and decreases the contact angle of nicotine with an adhesive, and the present invention can be practiced. From the aspect of compatibility with the adhesive, an organic liquid ingredient is preferable, and a lipophilic organic liquid ingredient is more preferable. When a drug is concurrently contained, one having an absorption promoting action may be used to improve transdermal absorbability. As the liquid ingredient, for example, fats and oils such as olive oil, castor oil, squalene, lanoline and the like; organic solvents such as dimethyldecyl sulfoxide, methyloctyl sulfoxide, dimethyl sulfoxide, dimethylformamide, dimethylacetamide, dimethyllaurylamide, methylpyrrolidone, dodecylpyrrolidone and the like; liquid surfactants; diisopropyl adipate, phthalic acid (di)ester (e.g., diisononyl phthalate, di(2-ethylhexyl) phthalate and the like), plasticizers such as diethyl sebacate and the like; hydrocarbons such as liquid paraffin; fatty acid esters such as fatty acid alkyl ester (e.g., alcohol wherein the alkyl moiety is linear, branched chain or cyclic alkyl having 1 to 13 carbon atoms, ester with saturated or unsaturated fatty acid having 8 to 18 carbon atoms and the like, specifically, ethyl oleate, isopropyl palmitate, octyl palmitate, isopropyl myristate, isotridecyl myristate, ethyl laurate and the like), glycerol fatty acid ester (e.g., ester of glycerol and saturated or unsaturated fatty acid having 8 to 16 carbon atoms and the like, specifically, caprylic.capric triglyceride and the like), propylene glycol fatty acid ester (e.g., ester of propylene glycol and saturated or unsaturated fatty acid having 8 to 16 carbon atoms, and the like, specifically, propylene glycol dicaprylate and the like), pyrrolidonecarboxylic acid alkyl ester and the like; aliphatic dicarboxylic acid alkyl ester (e.g., ester of alcohol wherein the alkyl moiety is a linear, branched chain or cyclic alkyl having 1 to 4 carbon atoms and saturated or unsaturated aliphatic dicarboxylic acid having 6 to 16 carbon atoms, and the like, specifically, diisopropyl adipate, diethyl sebacate and the like); polyhydric alcohol such as glycerol and the like; higher alcohol such as octyldodecanol and the like; silicone oil; ethoxylated stearyl alcohol and the like can be mentioned. Of these, one or more kinds are used in combination. Diisopropyl myristate, isopropyl palmitate, glycerol fatty acid ester are preferable, and of the glycerol fatty acid esters, caprylic.capric triglyceride is more preferable.

The caprylic.capric triglyceride is a triester of caprylic acid and capric acid, and glycerol. In the present invention, while the ratio of caprylic acid to capric acid is not particularly limited, caprylic acid:capric acid is generally about 5:5-about 9:1 (weight ratio). The caprylic.capric triglyceride may be a commercially available product (e.g., Coconad MT (manufactured by Kao Corporation) and the like).

As the liquid ingredient, fatty acid alkyl ester, especially isopropyl myristate, is preferable particularly from the aspect of good transdermal absorbability. Particularly, from the aspect of good adhesion, glycerol fatty acid ester, especially caprylic.capric triglyceride, is preferable. Particularly, good adhesion can be afforded and appropriate transdermal absorbability, which is not too high or too low, can be afforded, for example, in the aforementioned stop-smoking program (especially, a one time/day adhesion program), as a result of which the nicotine blood concentration can be maintained at a constant level for a long time by one time adhesion. From such aspect, a system including coexistence of isopropyl myristate and caprylic.capric triglyceride is preferable.

While the content ratio of isopropyl myristate and caprylic.capric triglyceride, when they are coexistent, is not particularly limited, it is particularly isopropyl myristate:caprylic.capric triglyceride=about 1:8-2:1 (weight ratio), from the aspect of achieving appropriate transdermal absorbability and good adhesion.

The content ratio of the liquid component is preferably 20-65 wt % relative to the whole adhesive layer, and from the aspect of skin irritation, it is more preferably 30-60 wt %.

Particularly, when the content ratio of the liquid ingredient falls within the above-mentioned preferable range, a nicotine transdermal preparation wherein the aforementioned contact angle of nicotine with an adhesive layer before containing nicotine falls within the above-mentioned range at any point in time from one second to 180 seconds from the start of the contact can be obtained. When the content ratio of the liquid component falls within the above-mentioned preferable range, moreover, a nicotine transdermal preparation wherein the adhesive properties of adhesive force, coagulation, tack and the like are well-balanced, or a nicotine transdermal preparation showing highly superior skin adhesion and less pain upon peeling off can be obtained.

The present inventors have also found that, when the same liquid ingredient as that to be added to the adhesive is mixed with nicotine and applied, the contact angle of nicotine with the adhesive decreases. A greater amount of the liquid ingredient to be added can decrease the contact angle, where an extremely large amount unpreferably requires a large amount of liquid to be applied to ensure that a determined amount of nicotine is applied. When the amount of liquid component to be added is extremely small, the effect of decreasing the contact angle becomes slim. Accordingly, when the liquid ingredient is to be added to nicotine, the proportion of the liquid ingredient is preferably 1-50 wt %, more preferably 5-30 wt %, still more preferably 10-20 wt %, relative to the whole mixture of nicotine and the liquid component.

The thickness of the adhesive layer is preferably 60-240 μm, and more preferably 80-120 μm from the aspects of skin adhesion and transdermal absorbability of nicotine.

In the present invention, the adhesive layer is preferably crosslinked to provide a suitable cohesion when applied to the skin of human and the like and to easily retain a liquid ingredient in the adhesive layer. As the crosslinking treatment, for example, a chemical crosslinking treatment using a crosslinking agent, such as an isocyanate compound (e.g., CORONATE HL (trade name, manufactured by Nippon Polyurethane Industry Co., Ltd.) and the like), a metal chelate compound (e.g., metal chelate compound made of titanium, zirconium, zinc or aluminum, specifically aluminum ethylacetoacetate.diisopropylate (e.g., ALCH (trade name, manufactured by Kawaken Fine Chemicals Co., Ltd.) and the like)), organic peroxide, an epoxy compound, a melamine resin, and the like, and a crosslinking treatment using UV, γ ray, electron beam and the like can be mentioned. Of these, a chemical crosslinking treatment using a crosslinking agent, such as an isocyanate compound, or a metal alcoholate or metal chelate compound consisting of titanium, zirconium, zinc, aluminum and the like is preferable from the aspects of reactivity and handling property. These crosslinking agents are free of a thickening phenomenon of the solution until application and drying, and are extremely superior in workability.

The amount of the crosslinking agent is about 0.01-5 parts by weight, per 100 parts by weight of the adhesive. When the amount of the crosslinking agent is too small, desired coagulation cannot be imparted to an adhesive layer because the number of crosslinking points is too small, and adhesive residue due to cohesive failure and strong skin irritation occur during peeling off. On the other hand, when the amount of the crosslinking agent is too high, coagulation grows but sufficient skin adhesion cannot be afforded and unreacted initiator may remain, which in turn may cause skin irritation and decomposition of nicotine and concomitant drug.

While the support is not particularly limited and any known support can be used, nicotine contained in the adhesive layer is preferably not lost from the back through the support to cause low content. Accordingly, the support is preferably made from a material impermeable to nicotine. When a drug other than nicotine is to be contained in the adhesive layer, it is preferable that the support be made of a material also impermeable to the drug. Specifically, a single film of polyester, nylon, saran, polyethylene, polypropylene, ethylenevinyl acetate copolymer, polyvinyl chloride, ethylene-ethyl acrylate copolymer, polytetrafluoroethylene, metal foil, polyethylene terephthalate and the like, a laminate film wherein one or more kinds thereof are laminated and the like can be used. To improve adhesion (anchor property) between the support and the adhesive layer, the support is, from among these, preferably a laminate sheet of a non-porous sheet made from the above-mentioned material and the following porous sheet, and the adhesive layer is preferably formed on the porous sheet side. The porous sheet is not particularly limited as long as the anchor property between the support and the adhesive layer can be improved and, for example, paper, woven fabric, non-woven fabric (e.g., polyester non-woven fabric, polyethylene terephthalate non-woven fabric and the like), a sheet obtained by a mechanical perforation treatment of the above-mentioned film and the like can be mentioned. Particularly, paper, woven fabric, non-woven fabric are preferable. The thickness of the support is generally within the range of 10-500 μm, in consideration of the improvement of anchor property and flexibility of the whole preparation.

When a woven fabric or a non-woven fabric is used as a porous sheet, the amount of the fabric weight is preferably 5-50 g/m², more preferably 8-40 g/m², for the improvement of anchor property.

In the present invention, the adhesive layer may be formed on a release liner. In this case, an adhesive layer may be formed on a release liner, the adhesive layer is impregnated with nicotine, and a support may be adhered to the surface of the adhesive layer, which is opposite to the release liner.

The nicotine transdermal preparation of the present invention can be produced by the production method of the nicotine transdermal preparation of the present invention described in detail in the following.

The method of the present invention is a method of producing a nicotine transdermal preparation comprising a support and an adhesive layer formed thereon, which layer comprising nicotine and a liquid ingredient compatible with the adhesive, which comprises (1) providing the adhesive layer wherein a contact angle of nicotine with an adhesive layer before containing nicotine is 20-60° (hereinafter to be referred to as step (1)), and applying nicotine to the adhesive layer to allow absorption of nicotine by the adhesive layer (hereinafter to be referred to as step (2)).

Step (1)

The "adhesive layer containing a liquid ingredient compatible with the adhesive" can be obtained, for example, by thoroughly stirring a mixed solution of an adhesive and a liquid component and, where necessary, a crosslinking agent, applying the solution on a support or release liner and drying same. Thereafter, where necessary, a crosslinking treatment is applied such as heating and the like. Using the aforementioned preferable ones for "an adhesive" and "a liquid ingredient compatible with the adhesive", an adhesive layer wherein a contact angle of nicotine with an adhesive layer before containing nicotine is 20-60° can be obtained.

Step (2)

Nicotine is applied to an adhesive surface of the adhesive layer. Then, nicotine is quickly absorbed into the adhesive layer.

Since nicotine shows the same level of viscosity as does water at ambient temperature, nicotine can be appropriately applied to an adhesive layer by a conventional liquid application technique. Accordingly, in the present invention, a nicotine transdermal preparation can be produced by preparing, in advance, an adhesive layer free of nicotine, and directly applying nicotine to the adhesive layer or impregnating the adhesive layer with nicotine by a known printing technique and the like, without heating nicotine having high volatility.

According to the method of the present invention, since nicotine is quickly absorbed into an adhesive layer after application of nicotine to the adhesive layer, the nicotine content does not vary much at any part of the bulk of the preparation of the present invention to be produced. As a result, continuous production of the nicotine transdermal preparation of the present invention superior in content uniformity can be enabled.

As a preferable embodiment of the production method of the nicotine transdermal preparation of the present invention, the following methods can be mentioned. A mixed solution of an adhesive and a liquid ingredient, and where necessary, a crosslinking agent is thoroughly stirred, the solution is applied to a support or release liner, and dried. Then, the release liner or support is adhered, and where necessary, a crosslinking treatment such as heating and the like is applied. Then, the release liner is peeled off, nicotine is directly applied onto the adhesive layer, and a different release liner is adhered thereto as appropriate. When adhering the different release liner, it is also possible to form a different adhesive layer and laminate the layer on the adhesive layer containing nicotine. The different adhesive layer to be laminated may have the same composition as the adhesive layer containing nicotine, or have a different composition.

As a method for directly applying nicotine to the adhesive, a thin film coating, particularly a printing technique employed in the printing field can also be used.

Nicotine (particularly nicotine free base) is a highly volatile drug, to which drying by heating is difficult to apply. However, according to the method of the present invention, since nicotine or a mixture of nicotine and a liquid ingredient is quickly absorbed after application to an adhesive layer, drying by heating after application is not necessary, and therefore, there is no concern about nicotine volatilization.

Examples of the method for applying nicotine include a method using a gravure coater, flexo coater, calendar coater, spray coater, curtain coater, fountain coater, die coater or slit die coater, inkjet and the like.

These methods can be adapted to thin film coating that general requires high precision, and when the content uniformity of a drug is required as in the present invention, such a coating method is advantageously employed. Moreover, since nicotine is used as it is as a coating solution at this time in the present invention, a coating method, wherein even a coating solution having a low viscosity can afford a high precision coating, is preferable. Moreover, since nicotine is extremely toxic, a highly safe coating method to a manufacturer is desirable, and therefore, a closed coating method is desirable. From such aspect, a method using a die coater or an inkjet printer of piezo system is particularly preferable, because of superior coating precision and easiness of making a closed system.

In the present invention, the most preferable method to apply nicotine is a method using a die coater, as shown below.

FIG. 1A and FIG. 1B show schematic views of one embodiment of die coating usable in the present invention.

Nicotine is supplied to die 3 from a nicotine supply tank 1 using a measuring pump 2. An adhesive layer 5 containing a liquid ingredient, which is supported by a support layer or a release liner, passes through a gap between a backup roll 4 and the die 3, and nicotine is uniformly applied to the adhesive layer 5 from the die 3.

As the die, for example, a curtain die, an ultra die, a lip die, a slot die and the like can be mentioned, with preference given to a slot die since it enables high precision coating with a low viscosity solution.

As the measuring pump, for example, a syringe pump, a gear pump, a mohno pump, a diaphragm pump and the like can be mentioned. In view of high precision and the like, a syringe pump is preferable, and a gear pump is also preferable.

The measurement precision of a pump is an important factor influencing the uniformity of nicotine application.

Not to mention the kind of measuring pump, the motor that drives the pump is also important, and a servo-type motor less susceptible to variation in the speed of rotation due to disturbance is preferably used.

In addition, the precision of the line speed of the adhesive layer 5 during application of nicotine is also important. The application amount of nicotine and application precision can be roughly determined based on the ratio of the speed of rotation and rotation precision of the measuring pump and the line speed alone. According to the production method of the present invention, since the nicotine absorption rate is sufficiently fast, the precision of the ratio of the speed of rotation of the measuring pump and the line speed can directly become the application precision.

As other factors influencing the uniformity of nicotine application, the pressure variation inside the nicotine supply line and the rheological characterization of nicotine inside the die can be mentioned. The pressure variation in the nicotine supply line may be caused by invasion of air bubbles into the supply line, besides the precision of the measurement pump. Thus, it is desirable to remove air bubbles inside the nicotine supply line. When a backup roll 4 is installed to keep the rotation axis horizontal so that the air bubbles can be easily removed, nicotine is desirably supplied from the intersection of the horizontal plane passing the rotation axis of the backup roll 4 and the outer circumference of the backup roll 4 or from the downstream in the rotation direction of the backup roll 4 (see FIG. 1A and FIG. 1B), and an air bubble trap (not shown) is desirably provided during the line. The pipe of a nicotine supply line 6 is desirably thin to facilitate removal of the air bubble. While the design of the diameter of the pipe varies depending on the supply amount of nicotine, when the nicotine supply amount is about 3 mL/min, the inner diameter of the pipe is desirably 2-4 mm. While the material of the pipe may be any as long as it is not corroded by nicotine, stainless is desirable since nicotine is poisonous. Even when the material of the pipe can be corroded by nicotine, a coating resistant to corrosion by nicotine can be applied to the inside of the pipe. It is preferable to use a Teflon (trade mark) pipe for confirmation of air bubbles inside the pipe.

A coating solution having low viscosity such as nicotine is considered to be hardly influenced by concaves and convexes on an adhesive surface and a slight variation of backup roll. Accordingly, the surface of the side to be applied may have concaves and convexes of at least about ±5 µm.

In the present invention, since nicotine is directly used as a coating solution without dissolving in conventional solubilizers such as a solvent and the like (e.g., Eudragit E-100 (aminoalkylmethacrylate copolymer E), manufactured by Röhm), the coating solution has a low viscosity and the speed of coating line can be increased. Accordingly, the present invention is highly advantageous for improving producibility and coating precision.

In the present invention, nicotine is not dissolved in an auxiliary substance such as a solvent and the like but directly used as a coating solution. As a result, the coating solution has low viscosity, and the application line speed can be raised. Consequently, the present invention is extremely advantageous for improving producibility and application precision.

The rheological characteristic of the coating solution in a die is also important for uniform application. Particularly, since the uniformity in the width direction of a wide die depends on the structure inside the die, a die sufficiently designed for nicotine application, which is of the level for general low viscosity use, is preferably used.

The gap (shim) of the die for application of nicotine can be adjusted with a metal film or a plastic film inactive with nicotine. As a metal film inactive with nicotine, a stainless film, a zinc foil film, a titanium foil film and the like can be mentioned. As a plastic film inactive with nicotine, a polyethylene terephthalate film, a Teflon (trade mark) film, a cellulose acetate film, a polyvinyl chloride film, a polyethylene film, a polypropylene film, a polycarbonate film, a polyamide film and the like can be mentioned. The most preferable materials of shim include a polyethylene terephthalate film and a stainless film. While the thickness of the shim varies depending on the application thickness and speed of the application line, when the application thickness is 15-20 µm, it is preferably 20 µm-100 µm.

Specific examples of the die system include slot die systems manufactured by LIBERTY, US and CLOEREN, US. However, the die system usable in the present invention is not limited to these. In addition, slot die systems manufactured by Chugai Ro Co., Ltd. and TORAY Engineering Co., Ltd., including measuring pumps, and the like can also be used preferably.

As mentioned above, since the application precision is determined based solely on the ratio of the speed of rotation of the measuring pump and the line speed in the nicotine application of the present invention, a device to control electric signals between the measuring pump and the line speed, and feedback the speed of rotation may be set, which is preferably designed to automatically increase the speed of rotation of the pump at a constant ratio as the line speed is increased.

Moreover, since the coating solution is poisonous, it is desirable to install a mechanism that automatically washes the head, inside, pipe and tank of the die. In addition, a safety cover may be set on a nicotine exposure part, or a ventilation device may be set in a workroom, to prepare for the occurrence of evaporation from the nicotine exposure surface.

In the present invention, nicotine is generally applied at room temperature. Inasmuch an indoor temperature change results in variation of specific gravity of nicotine, which in turn leads to the variation in the application amount, the temperature of nicotine to be applied is preferable maintained at a constant level. To maintain a constant temperature of nicotine, a device to maintain the temperatures of die, pipe and tank at constant levels may be equipped. When nicotine is applied at a high temperature, the infiltration speed of nicotine into an adhesive layer becomes high, though volatilization of nicotine places workers in danger. Accordingly, for safety of workers, nicotine application at a low temperature is preferable, and the temperature of nicotine is maintained at 0-40° C., preferably 5-30° C., more preferably 10-25° C. The temperature change is preferably within ±2° C.

Since nicotine is hygroscopic, a long-term preservation in a highly humid place without humidity management should be preferably avoided. However, extremely low humidity may lead to inflammation and explosion of nicotine due to static spark. Therefore, nicotine is desirably applied at a place humidity-conditioned to a constant humidity (relative humidity 40-60%).

The shape and the size of the nicotine transdermal preparation of the present invention are not particularly limited, and any shape and size can be employed according to the adhesion site and the like. The shape includes, for example, tape, sheet and the like. The size of the preparation is, for example, 5-30 $cm^2$.

The nicotine transdermal preparation of the present invention can be used for a nicotine supplement therapy and the like of smokers (particularly those wishing to quit smoking), according to a stop-smoking program conventionally practiced or to be practiced in the future, which aims at suppressing habitual smoking.

While the dose of nicotine by the nicotine transdermal preparation of the present invention varies depending on the age and body weight of the patients, severity of disease and the like, a transdermal preparation containing 5-120 mg of nicotine is generally adhered to the skin (5-30 $cm^2$) of an adult once or so per 0.5 to 2 days.

EXAMPLES

The present invention is explained in detail in the following by referring to Examples, which are not to be construed as limitative. Unless otherwise specified, part and % mean parts by weight and wt %, respectively, in the following.

Example 1

Under a nitrogen atmosphere, 2-ethylhexyl acrylate (95 parts), acrylic acid (5 parts), ethyl acetate (100 parts) and benzoyl peroxide (0.2 part) were reacted in a separable flask equipped with a refluxing condenser, a stirrer, a thermometer, a dropping funnel and a nitrogen inlet tube at 60° C. for 15 hr to give an adhesive solution (to be abbreviated as Acryl 1).

The obtained adhesive solution was measured out in an amount corresponding to adhesive solid content of 59.92 parts and placed in a reaction container. Isopropyl myristate was added to the reaction container in 40 parts relative to the adhesive solid content, CORONATE HL (manufactured by Nippon Polyurethane Industry Co., Ltd.) was added as a crosslinking agent in a proportion of 0.08 part (0.14% of the adhesive), and the mixture was thoroughly stirred.

The obtained solution was applied to a peel treated surface of a polyethylene terephthalate film release liner having the peel treated surface on one side to a thickness after drying of 240 μm, and dried at 60° C. for 3 min, 80° C. for 3 min and 95° C. for 3 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate. The laminate was tightly sealed, left standing at 60° C. for 48 hr to form a crosslinked adhesive layer.

Thereafter, free base nicotine was applied to the adhesive surface of the adhesive layer with a die coater, while peeling off the release liner of the laminate to expose the adhesive surface. Then, a polyethylene terephthalate release liner was adhered to the nicotine-coated surface to give a nicotine transdermal preparation bulk (width 100 mm, length 15 m).

Examples 2-4

Under a nitrogen atmosphere, 2-ethylhexyl acrylate (72 parts), N-vinyl-2-pyrrolidone (25 parts) and acrylic acid (3 parts) were charged in a flask, azobisisobutyronitrile (0.3 part) was added as a polymerization initiator, and polymerization was started. By adjusting the stirring rate and the outer bath temperature, and dropwise addition of ethyl acetate, the bath inner temperature was controlled to 58-62° C., and a polymerization reaction was carried out to give an adhesive solution (to be abbreviated as Acryl 2).

In Examples 2, 3 and 4, as shown in Table 1, the above-mentioned adhesive solution was measured out in an amount corresponding to an adhesive solid content of 69.79, 59.82 or 49.85 parts and placed in a reaction container. Isopropyl palmitate was added to the reaction container in a proportion of 30, 40 or 50 parts relative to the adhesive solid content, furthermore ALCH (manufactured by Kawaken Fine Chemicals Co., Ltd. aluminum ethylacetoacetate diisopropylate) as a crosslinking agent was added 0.3% of the adhesive and the mixture was thoroughly stirred. The obtained solution was applied to a peel treated surface of a polyethylene terephthalate film release liner having the peel treated surface on one side to a thickness after drying of 120 μm, and dried at 70° C. for 2 min and 90° C. for 2 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate. The laminate was tightly sealed, left standing at 60° C. for 48 hr to form a crosslinked adhesive layer, whereby the crosslinked adhesive layers of Examples 2-4 were prepared.

Thereafter, free base nicotine was applied to the adhesive surface of the adhesive layer with a die coater, while peeling off the release liner of the laminate to expose the adhesive surface. Then, a polyethylene terephthalate release liner was adhered to the nicotine-coated surface to give a nicotine transdermal preparation bulk (width 100 mm, length 15 m).

Examples 5-8

DURO-TAK2196 (manufactured by National Starch & Chemical Company, to be abbreviated as Acryl 3) was measured out in an amount corresponding to the adhesive solid content of 79.68, 69.72, 59.76 or 49.80 parts and placed in a reaction container. Coconad MT (manufactured by Kao Corporation, caprylic.capric triglyceride) was added to the reaction container in a proportion of 20, 30, 40 or 50 parts relative to the adhesive solid content, ALCH (manufactured by Kawaken Fine Chemicals Co., Ltd. aluminum ethylacetoacetate.diisopropylate) as a crosslinking agent was added 0.4% of the adhesive and the mixture was thoroughly stirred.

The obtained solution was applied to a peel treated surface of a polyethylene terephthalate film release liner having the peel treated surface on one side to a thickness after drying of 80 μm, and dried at 70° C. for 2 min and 90° C. for 2 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate. The laminate was tightly sealed, left standing at 60° C. for 48 hr to form a crosslinked adhesive layer, whereby the crosslinked adhesive layers of Examples 5-8 were prepared.

Thereafter, free base nicotine was applied to the adhesive surface of the adhesive layer with a die coater, while peeling off the release liner of the laminate to expose the adhesive surface. Then, a polyethylene terephthalate release liner was adhered to the nicotine-coated surface to give a nicotine transdermal preparation (width 100 mm, length 14 m).

Example 9

In the same manner as in Example 2 except that isopropyl myristate (30 parts relative to adhesive solid content) was used instead of the isopropyl palmitate (30 parts relative to adhesive solid content), a nicotine transdermal preparation was obtained.

Examples 10 and 11

Under a nitrogen atmosphere, 2-ethylhexyl acrylate (72 parts), N-vinyl-2-pyrrolidone (25 parts) and acrylic acid (3 parts) were charged in a flask, azobisisobutyronitrile (0.3 part) was added as a polymerization initiator, and polymerization was started. By adjusting the stirring rate and the outer bath temperature, and dropwise addition of ethyl acetate, the bath inner temperature was controlled to 58-62° C., and a polymerization reaction was carried out to give an adhesive solution (Acryl 2).

In Examples 10 and 11, as shown in Table 1, the above-mentioned adhesive solution was measured out in an amount corresponding to an adhesive solid content of 39.88 or 29.91 parts and placed in a reaction container. isopropyl myristate was added to the reaction container in a proportion of 60 or 70 parts relative to the adhesive solid content, ALCH (manufactured by Kawaken Fine Chemicals Co., Ltd. aluminum ethylacetoacetate diisopropylate) as a crosslinking agent was added 0.3% of the adhesive and the mixture was thoroughly stirred. The obtained solution was applied to a peel treated surface of a polyethylene terephthalate film release liner having the peel treated surface on one side to a thickness after drying of 70 μm, and dried at 70° C. for 2 min and 90° C. for 2 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate. The laminate was tightly sealed, left standing at 60° C. for 48 hr to form a crosslinked adhesive layer, whereby crosslinked adhesive layers of Examples 10 and 11 were prepared.

Thereafter, the release liner was peeled off to expose an adhesive surface, an engraving roller (applied amount: Calculated 30 mg/cm$^2$) was set on a flexo printing coater (manufactured by RK Print Coat Instruments Ltd., trade name: K-rocks proofer), and a nicotine free base (manufactured by Sigma) was directly applied to an adhesive surface of the adhesive layer to give a nicotine-containing transdermal preparation. The coating speed was constantly 0.1 m/min.

Comparative Example 1

The adhesive solution (Acyrl 1) obtained in Example 1 was directly (i.e., without liquid ingredient) applied to a peel treated surface of a polyethylene terephthalate film release liner having the peel treated surface on one side to a thickness after drying of 240 μm, and dried at 60° C. for 3 min, 80° C. for 3 min and 95° C. for 3 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate.

Comparative Example 2

The adhesive solution (Acryl 2) obtained in Example 2 was directly (i.e., without liquid ingredient) applied to a peel treated surface of a polyethylene terephthalate film release liner having the peel treated surface on one side to a thickness after drying of 120 μm, and dried at 70° C. for 2 min and 90° C. for 2 min to give an adhesive layer. The adhesive surface of the adhesive layer thus formed was adhered to the surface on a non-woven fabric side of a support prepared by laminating a 2 μm thick polyethylene terephthalate film on the polyester non-woven fabric (fabric weight amount 12 g/m$^2$) by extrusion forming to give a laminate.

Thereafter, free base nicotine was applied to the adhesive surface of the adhesive layer with a die coater, while peeling off the release liner of the laminate. Then, a polyethylene terephthalate release liner was adhered to the nicotine-coated surface to give a nicotine transdermal preparation (width 100 mm, length 11 m).

Comparative Example 3

DURO-TAK 2196 (Acryl 3) used in Example 5 was directly (without a liquid component) applied to a peel-treated surface of a polyethylene terephthalate release liner subjected to a peel treatment of only one surface, such that the thickness after drying became 80 μm, dried at 70° C. for 2 minutes, then at 90° C. for 2 minutes to form an adhesive layer. The adhesive surface of the formed adhesive layer was adhered to a non-woven fabric side of a support prepared by laminating a 2 μm-thick polyethylene terephthalate film on a polyester non-woven fabric (fabric weight amount 12 g/m$^2$) by extrusion forming, whereby an adhesive layer was prepared.

Comparative Example 4

An adhesive solution (74 parts:6 parts:20 parts isooctyl acrylate:acrylamide:vinyl acetate copolymer, solid content in 91 parts:9 parts ethyl acetate:methanol 22%, inherent viscosity=1.21 dl/g) was applied to a peel-treated surface of a polyethylene terephthalate release liner with an extrusion die. The die had a 20 mil (500 μm) shim. The coated release liner was dried in an oven at 150° F. (65° C.) for 1 min., 275° F. (135° C.) for 1 min., then 350° F. (177° C.) for 1 min. to give a web (width 7 inches (17.8 cm), 4000 line yards (3640 line meters).

Using direct gravure coating [gravure roll parameter: pattern-triple helix; 45 line per inch (18 line per cm); volume factor $-3.0\times10^{-3}$ in$^3$/in$^2$ ($7.6\times10^{-3}$ cm$^3$/cm$^2$), nicotine was uniformly applied as it was (i.e., 0% polymer content) but failed.

TABLE 1

| | composition of adhesive layer | | | | | |
|---|---|---|---|---|---|---|
| | adhesive | | crosslinking agent | | liquid ingredient | |
| | kind | content ratio (wt %) | kind | content ratio (wt %) | kind | content ratio (wt %) |
| Ex. 1 | Acryl 1 | 59.92 | CORONATE HL | 0.08 | IPM | 40 |
| Ex. 2 | Acryl 2 | 69.79 | ALCH | 0.21 | IPP | 30 |
| Ex. 3 | Acryl 2 | 59.82 | ALCH | 0.18 | IPP | 40 |
| Ex. 4 | Acryl 2 | 49.85 | ALCH | 0.15 | IPP | 50 |
| Ex. 5 | Acryl 3 | 79.68 | ALCH | 0.32 | MT | 20 |
| Ex. 6 | Acryl 3 | 69.72 | ALCH | 0.28 | MT | 30 |
| Ex. 7 | Acryl 3 | 59.76 | ALCH | 0.24 | MT | 40 |
| Ex. 8 | Acryl 3 | 49.80 | ALCH | 0.20 | MT | 50 |
| Ex. 9 | Acryl 2 | 69.79 | ALCH | 0.21 | IPM | 30 |
| Ex. 10 | Acryl 2 | 39.88 | ALCH | 0.12 | IPM | 60 |
| Ex. 11 | Acryl 2 | 29.91 | ALCH | 0.09 | IPM | 70 |
| Com. Ex. 1 | Acryl 1 | 100 | — | 0 | — | 0 |
| Com. Ex. 2 | Acryl 2 | 100 | — | 0 | — | 0 |
| Com. Ex. 3 | Acryl 3 | 100 | — | 0 | — | 0 |

IMP: isopropyl myristate
IPP: isopropyl palmitate
MT: Coconad MT (caprylic · capric triglyceride)

Experimental Example

The nicotine transdermal preparation samples obtained in Examples and Comparative Examples were subjected to the following evaluation.

Measurement of Contact Angle of Nicotine

The contact angle of nicotine with the adhesive layers prepared in Examples and Comparative Examples (crosslinked adhesive layer before nicotine application for Examples 1-11, an adhesive layer before nicotine application for Comparative Example 2, adhesive layer of the obtained preparations for Comparative Examples 1, 3) was measured by a contact angle measurement apparatus DropMaster 700 (manufactured by Kyowa Interface Science Co., LTD).

Measurement method: contact angle (droplet method)
Measurement range: contact angle:0-180°
Measurement precision: contact angle:±1°
Indicated resolution: contact angle:0.1°
Determination of Measurement Position: Operation on PC Screen
Preparation of quantitation droplet: automatic
Liquid landing control/Liquid landing recognition automatic
Contact angle analysis: automatic The (crosslinked) adhesive layers prepared in Examples and Comparative Examples were fixed on glass slides with the surface of the release liner facing upward and set on the apparatus. A release liner was peeled off and a nicotine droplet was contacted on an adhesive surface of the exposed adhesive layer, and the contact angle 1 second later was measured under the conditions of room temperature 23±2° C., relative humidity 60±10% RH. The amount of nicotine droplet was adjusted to 1.1 μL.

In addition, changes in the contact angle were measured with time at every about 9 seconds for about 3 minutes.

The results are shown in FIG. 2 and Table 2. From these results, changes in the contact angle of nicotine with the adhesive layers of Examples 1-11 were shown to be remarkably higher than those in Comparative Examples 1-3.

TABLE 2

|  | contact angle (°) after 1 second | contact angle (°) after 3 minutes | change (°) in contact angle | change (%) in contact angle | coating uniformity (visual) |
|---|---|---|---|---|---|
| Ex. 1 | 44.5 | 30.5 | 14.0 | 31.5 | ⊙ |
| Ex. 2 | 52.3 | 42.2 | 10.1 | 19.3 | ○ |
| Ex. 3 | 46.2 | 36.1 | 10.1 | 21.9 | ⊙ |
| Ex. 4 | 43.2 | 28.7 | 14.5 | 33.6 | ⊙ |
| Ex. 5 | 55.0 | 41.3 | 13.7 | 24.9 | ○ |
| Ex. 6 | 49.2 | 35.7 | 13.5 | 27.4 | ⊙ |
| Ex. 7 | 46.8 | 30.3 | 16.5 | 35.3 | ⊙ |
| Ex. 8 | 45.6 | 25.8 | 19.8 | 43.4 | ⊙ |
| Ex. 9 | 52.5 | 44.2 | 8.3 | 15.8 | ○ |
| Ex. 10 | 31.5 | 12.1 | 19.4 | 61.6 | ⊙ |
| Ex. 11 | 38.9 | 18.3 | 20.6 | 53.0 | ⊙ |
| Com. Ex. 1 | 66.0 | 60.4 | 5.6 | 8.5 | x |
| Com. Ex. 2 | 67.7 | 66.0 | 1.7 | 2.5 | x |
| Com. Ex. 3 | 68.3 | 60.2 | 8.1 | 11.9 | x |

Change (°) in contact angle = (contact angle after 1 second) − (contact angle after 3 minutes)
Change (%) in contact angle = {(change (°) in contact angle)/(contact angle after 1 second)} × 100
⊙: No repellency, nicotine could be easily applied uniformly.
○: Slight degree of repellency was observed but nicotine could be applied uniformly.
x: Repellency was markedly observed and nicotine could not be applied uniformly.

Change (°) in contact angle=(contact angle after 1 second)−(contact angle after 3 minutes)

Change (%) in contact angle={(change (°) in contact angle)/(contact angle after 1 second)}×100

⊙: No repellency, nicotine could be easily applied uniformly.
○: Slight degree of repellency was observed but nicotine could be applied uniformly.
x: Repellency was markedly observed and nicotine could not be applied uniformly.

Nicotine Content

From the nicotine transdermal preparations obtained in Examples 1, 3 and 6 and Comparative Example 2, samples were obtained at 2 points (front and rear in Tables 3-5) at 25 mm from the both ends in the width direction of the area coated with nicotine as the center, and 18-21 points at 0.5 m intervals in the coating direction. For sampling, a 10 cm² square punching mold was used, and the nicotine transdermal preparation samples were punched out, extracted by shaking in methanol at room temperature for 120 min shaking (about 90 rpm), and quantified for the nicotine content of the extract by HPLC.

The results are shown in Tables 3-6. As is clear from these results, the variation in the nicotine content of the preparations of Examples 1, 3 and 6 was remarkable smaller than that in Comparative Example 2, and the preparation of the present invention is superior in content uniformity.

TABLE 3

Variation in nicotine content of preparation of Example 1

| | nicotine content (mg/cm²) | |
|---|---|---|
| coating (m) | front | rear |
| 0.0 | 1.75 | 1.74 |
| 0.5 | 1.69 | 1.72 |
| 1.0 | 1.71 | 1.69 |
| 1.5 | 1.72 | 1.73 |
| 2.0 | 1.69 | 1.72 |
| 2.5 | 1.67 | 1.67 |
| 3.0 | 1.7 | 1.65 |
| 3.5 | 1.67 | 1.67 |
| 4.0 | 1.66 | 1.68 |
| 4.5 | 1.65 | 1.65 |
| 5.0 | 1.65 | 1.65 |
| 5.5 | 1.69 | 1.64 |
| 6.0 | 1.68 | 1.74 |
| 6.5 | 1.74 | 1.73 |
| 7.0 | 1.74 | 1.71 |
| 7.5 | 1.7 | 1.73 |
| 8.0 | 1.71 | 1.71 |
| 8.5 | 1.72 | 1.74 |
| 9.0 | 1.64 | 1.73 |
| 9.5 | 1.67 | 1.74 |
| 10.0 | 1.63 | 1.67 |
| average | 1.70 | |
| standard deviation | 0.035 | |
| relative standard deviation | 2.0 | |

TABLE 4

Variation in nicotine content of preparation of Example 3

| | nicotine content (mg/cm²) | |
|---|---|---|
| coating (m) | front | rear |
| 0.0 | 1.82 | 1.85 |
| 0.5 | 1.8 | 1.83 |
| 1.0 | 1.87 | 1.89 |
| 1.5 | 1.87 | 1.87 |
| 2.0 | 1.83 | 1.87 |
| 2.5 | 1.87 | 1.88 |
| 3.0 | 1.87 | 1.88 |
| 3.5 | 1.83 | 1.88 |
| 4.0 | 1.84 | 1.84 |
| 4.5 | 1.88 | 1.88 |
| 5.0 | 1.88 | 1.89 |
| 5.5 | 1.86 | 1.87 |
| 6.0 | 1.9 | 1.87 |
| 6.5 | 1.89 | 1.87 |
| 7.0 | 1.9 | 1.87 |
| 7.5 | 1.86 | 1.89 |
| 8.0 | 1.83 | 1.87 |
| 8.5 | 1.85 | 1.88 |

TABLE 4-continued

Variation in nicotine content of preparation of Example 3

| coating (m) | nicotine content (mg/cm²) | |
|---|---|---|
| | front | rear |
| 9.0 | 1.88 | 1.88 |
| 9.5 | 1.88 | 1.87 |
| 10.0 | 1.86 | 1.88 |
| average | 1.87 | |
| standard deviation | 0.022 | |
| relative standard deviation | 1.2 | |

TABLE 5

Variation in nicotine content of preparation of Example 6

| coating (m) | nicotine content (mg/cm²) | |
|---|---|---|
| | front | rear |
| 0.0 | 1.64 | 1.56 |
| 0.5 | 1.65 | 1.57 |
| 1.0 | 1.67 | 1.60 |
| 1.5 | 1.68 | 1.59 |
| 2.0 | 1.66 | 1.63 |
| 2.5 | 1.63 | 1.68 |
| 3.0 | 1.70 | 1.62 |
| 3.5 | 1.70 | 1.63 |
| 4.0 | 1.70 | 1.63 |
| 4.5 | 1.64 | 1.71 |
| 5.0 | 1.64 | 1.66 |
| 5.5 | 1.70 | 1.65 |
| 6.0 | 1.70 | 1.67 |
| 6.5 | 1.70 | 1.61 |
| 7.0 | 1.70 | 1.67 |
| 7.5 | 1.71 | 1.61 |
| 8.0 | 1.68 | 1.65 |
| 8.5 | 1.50 | 1.66 |
| 9.0 | 1.55 | 1.64 |
| 9.5 | 1.60 | 1.54 |
| 10.0 | 1.60 | 1.61 |
| average | 1.64 | |
| standard deviation | 0.051 | |
| relative standard deviation | 3.1 | |

TABLE 6

Variation in nicotine content of preparation of Comparative Example 2

| coating (m) | nicotine content (mg/cm²) | |
|---|---|---|
| | front | rear |
| 0.0 | 1.70 | 1.64 |
| 0.5 | 1.59 | 1.66 |
| 1.0 | 1.56 | 1.51 |
| 1.5 | 1.74 | 1.81 |
| 2.0 | 1.54 | 1.48 |
| 2.5 | 1.60 | 1.59 |
| 3.0 | 1.62 | 1.62 |
| 3.5 | 1.66 | 1.63 |
| 4.0 | 1.73 | 1.75 |
| 4.5 | 1.54 | 1.61 |
| 5.0 | 1.47 | 1.65 |
| 5.5 | 1.46 | 1.65 |
| 6.0 | 1.42 | 1.62 |
| 6.5 | 1.45 | 1.63 |
| 7.0 | 1.45 | 1.64 |
| 7.5 | 1.39 | 1.61 |
| 8.0 | 1.36 | 1.59 |
| 8.5 | 1.41 | 1.57 |
| average | 1.58 | |
| standard deviation | 0.106 | |
| relative standard deviation | 6.7 | |

Evaluation of Adhesiveness

Adhesion:

The nicotine transdermal preparations bulk of Examples 1, 3, 6 and 9-11 and Comparative Example 2 were cut into samples having a width of 24 mm, and the adhesion force of the samples was evaluated using a bakelite board as a deposit and a tensile tester (EZTest, manufactured by Shimadzu Corporation). Evaluation of pain upon peeling off:

The nicotine transdermal preparations bulk of Examples 1, 3, 6 and 9-11 and Comparative Example 2 were formed into 10 cm² samples and adhered to the upper arm of 6 healthy volunteers for 24 hr. The pain upon peeling off of the preparations was evaluated according to the five level scores shown below.

1: not painful
2: only slightly painful
3: slightly painful
4: a little painful
5: very painful The results are shown in Table 7.

TABLE 7

| | liquid ingredient | | pain | falling off |
|---|---|---|---|---|
| name | content ratio (wt %) in adhesive layer | adhesive force (n = 3) N/24 mm average | upon peeling off average score | of sample in 6 volunteers during adhesion for 24 hr |
| Ex. 1 | isopropyl myristate | 40 | 1.9 | 1.1 | 0/6 |
| Ex. 3 | isopropyl palmitate | 40 | 2.3 | 1.2 | 0/6 |
| Ex. 6 | Coconad MT | 30 | 3.0 | 1.5 | 0/6 |
| Ex. 9 | isopropyl myristate | 30 | 2.6 | 1.4 | 0/6 |
| Ex. 10 | isopropyl myristate | 60 | 0.6 | 1.0 | 3/6 |
| Ex. 11 | isopropyl myristate | 70 | 0.5 | 1.0 | 4/6 |
| Com. Ex. 2 | — | 0 | 5.5 | 4.7 | 0/6 |

Evaluation of Skin Permeability

The drug permeability of the nicotine transdermal preparations produced by Examples 1, 3 and 6 was evaluated using the skin removed from hairless mouse and under the following conditions.

permeation apparatus: automated flow-through diffusion cell apparatus (manufactured by Vanguard International) sample area: 0.2826 cm² receptor solution: phosphate buffer (pH=7.4), containing 0.02% sodium azide flow: about 10 mL/4 hr/cell (pump rotation: 2.0 rpm) sampling points: 1, 2, 3, 4, 5, 6, 7, 8, 12, 16, 20, 24 hr samples: nicotine transdermal preparations of Examples 1-3 and 6 (each n=3)

As the comparison control, a commercially available nicotine transdermal preparation Nicotinell TTS 10 (manufactured by Novartis) was used.

Figure 3:
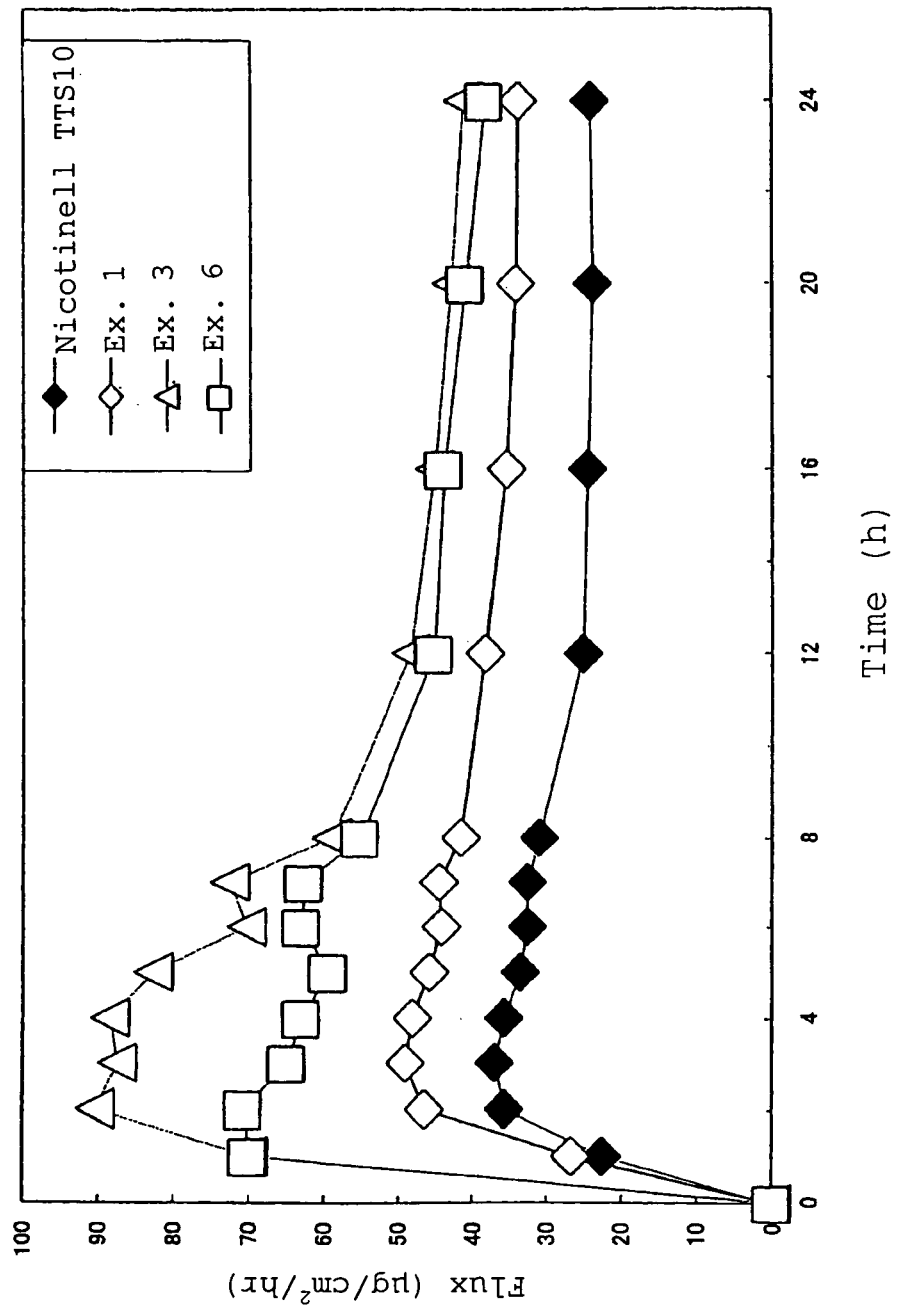
FIG. 3 is a graph showing the results of the skin permeability test (Flux) of Examples 1, 3 and 6 and comparison control (Nicotinell TTS10), in Experimental Example.

The content of nicotine flown into the receptor solution was quantified by HPLC. The results are shown in FIG. 3.

As shown in the above, the preparations of the present invention showed superior adhesion to the skin. They are preferable as a nicotine transdermal preparation to be adhered every day, since the pain upon peeling off is small and cause very small irritation. With no falling off during use, the preparations are highly economical. Moreover, the preparations of the present invention showed permeability of the same level as or not less than that of the existing nicotine transdermal preparations, as a result of the skin permeability test.

This application is based on a patent application No. 2005-299203 filed in Japan, the contents of which are incorporated in full herein by this reference.

The invention claimed is:

1. A method of producing a nicotine transdermal preparation comprising a support and an adhesive layer formed thereon, which adhesive layer comprising
    an acrylic adhesive
        comprising a main component which is (meth)acrylic acid alkyl ester and
        comprising a secondary monomer and a tertiary monomer both copolymerized with said main component, said second monomer being a monomer capable of being involved in a crosslinking reaction, said tertiary monomer comprising one or more kinds of monomer components selected from the group consisting of vinyl esters, vinyl ethers, vinyl amides, hydroxyl group-containing monomers, amido group-containing monomers, alkoxy group-containing monomers, and vinyl monomers,
    nicotine and
    a fatty acid alkyl ester or glycerol fatty acid ester,
which method comprises
    providing the adhesive layer wherein a contact angle of nicotine with the adhesive layer before containing nicotine is 20-60°, and
    continuously applying a coating solution consisting solely of nicotine to the adhesive layer with a die coater to allow absorption of nicotine into the adhesive layer, wherein the fatty acid alkyl ester or glycerol fatty acid ester is contained in a proportion of 40-65 wt % relative to the adhesive layer before containing nicotine.

2. The method of claim 1, wherein the adhesive layer is a crosslinked acrylic adhesive layer.

3. The method of claim 1, wherein the contact angle of nicotine with the adhesive layer before containing nicotine changes by not less than 15% between one second after dropwise addition of nicotine and 3 minutes after dropwise addition of nicotine.

4. The method of claim 1, wherein the contact angle of nicotine with the adhesive layer before containing nicotine changes by not less than 15% between one second after dropwise addition of nicotine and 3 minutes after dropwise addition of nicotine.

5. The method of claim 1, wherein the fatty acid alkyl ester or glycerol fatty acid ester is selected from the group consisting of isopropyl myristate, isopropyl palmitate, and caprylic-.capric triglyceride.

* * * * *

UNITED STATES PATENT AND TRADEMARK OFFICE
CERTIFICATE OF CORRECTION

PATENT NO. : 8,506,991 B2
APPLICATION NO. : 11/546302
DATED : August 13, 2013
INVENTOR(S) : Shiro Satoda et al.

It is certified that error appears in the above-identified patent and that said Letters Patent is hereby corrected as shown below:

In the Claims

Column 24, line 25, claim 4: delete "claim 1" and insert --claim 2--.

Signed and Sealed this
Eighteenth Day of March, 2014

Michelle K. Lee
*Deputy Director of the United States Patent and Trademark Office*